United States Patent
Bauer et al.

(10) Patent No.: US 9,422,213 B2
(45) Date of Patent: Aug. 23, 2016

(54) METHOD FOR PRODUCING DIMETHYL ETHER AND DEVICE SUITABLE THEREFOR

(71) Applicant: THYSSENKRUPP INDUSTRIAL SOLUTIONS AG, Essen (DE)

(72) Inventors: Melanie Bauer, Essen (DE); Harald Kömpel, Neu-Isenburg (DE); Alexander Schulz, Frankfurt (DE)

(73) Assignee: THYSSENKRUPP INDUSTRIAL SOLUTIONS AG, Essen (DE)

( * ) Notice: Subject to any disclaimer, the term of this patent is extended or adjusted under 35 U.S.C. 154(b) by 0 days.

(21) Appl. No.: 14/428,298

(22) PCT Filed: Sep. 10, 2013

(86) PCT No.: PCT/EP2013/002702
§ 371 (c)(1),
(2) Date: Mar. 13, 2015

(87) PCT Pub. No.: WO2014/040719
PCT Pub. Date: Mar. 20, 2014

(65) Prior Publication Data
US 2015/0232402 A1    Aug. 20, 2015

(30) Foreign Application Priority Data
Sep. 15, 2012  (DE) .......... 10 2012 018 341

(51) Int. Cl.
C07C 41/09 (2006.01)
C07C 41/42 (2006.01)
B01J 19/24 (2006.01)

(52) U.S. Cl.
CPC ............. *C07C 41/09* (2013.01); *B01J 19/245* (2013.01); *C07C 41/42* (2013.01); *B01J 2219/00103* (2013.01); *B01J 2219/24* (2013.01)

(58) Field of Classification Search
USPC ................. 568/471, 472, 618, 698
See application file for complete search history.

(56) References Cited

U.S. PATENT DOCUMENTS

| 4,560,807 A | 12/1985 | Murai et al. |
| 4,802,958 A | 2/1989 | Mazanec |
| 2009/0023958 A1 | 1/2009 | Jun et al. |

FOREIGN PATENT DOCUMENTS

| CN | 101903323 A | * 12/2010 | ............. B01J 8/0453 |
| DE | 102011114228 A1 | 3/2013 | |
| EP | 0270852 A2 | 6/1988 | |
| WO | 2006/041253 A1 | 4/2006 | |
| WO | 2013/041516 A2 | 3/2013 | |

OTHER PUBLICATIONS

German Language International Search Report for International patent application No. PCT/EP2013/002702; mailing date Feb. 21, 2014.
English Translation of International Search Report for International patent application No. PCT/EP2013/002702; mailing date Feb. 21, 2014.
English translation of abstract for CN 101903323 (A), Dec. 1, 2010.
English translation of abstract for DE 102011114228 (A1), Mar. 28, 2013.
Ullmann's Encyclopedia of Industrial Chemistry, Fifth Completely Revised Edition, vol. A8, pp. 541 to 544, of 1987.
English Language Abstract of EP0270852, 1998.
Farsi, Mohammad et al.; Modeling and Optimization of MeOH to DME in Isothermal Fixed-bed Reactor; International Journal of Chemical Reactor Engineering; 2010; pp. 1-14; vol. 8, Article A79; The Berkley Electronic Press, Berkeley, CA, USA.

* cited by examiner

*Primary Examiner* — Pancham Bakshi
(74) *Attorney, Agent, or Firm* — thyssenkrupp North America, Inc.

(57) ABSTRACT

The present disclosure relates to a method and apparatus for producing dimethyl ether by catalytic dehydration of methanol and by distillation of the dehydration product. The method is characterized in that the catalytic dehydration takes place in at least two reaction stages which are connected in series and of which at least the first reaction stage is operated adiabatically, wherein a cooling of the reaction products takes place at least between the first and the second reaction stages.

14 Claims, 2 Drawing Sheets

METHOD FOR PRODUCING DIMETHYL ETHER AND DEVICE SUITABLE THEREFOR

CROSS REFERENCE TO RELATED APPLICATIONS

This application is a U.S. National Stage Entry of International Patent Application Serial Number PCT/EP2013/002702, filed Sep. 10, 2013, which claims priority to German patent application no. DE 102012018341.0 filed Sep. 15, 2012, the entire contents of both of which are incorporated herein by reference.

FIELD

The invention relates to a process for preparing dimethyl ether and a reactor suitable for this purpose.

BACKGROUND

Dimethyl ether (hereinafter also referred to as "DME") is used in many fields in industrial production and by the private consumer. Examples are the use as propellant, e.g. for hair spray, or as starting material for chemical syntheses, e.g. for the preparation of dimethyl sulfate or light olefins (ethylene, propylene, butenes). In addition, DME is a low-emission fuel which is used as an alternative to liquefied petroleum gas from crude oil ("LPG") and can replace the latter in the long term. The use as low-emission fuel for diesel vehicles has also been tested successfully in a number of countries. DME is usually prepared from synthesis gas ($H_2$ and CO) obtained by reforming of natural gas or by gasification of coal or solids.

The preparation of dimethyl ether is then effected either by direct synthesis from synthesis gas or in two stages via the synthesis of methanol and subsequent conversion of the methanol into DME and water. The DME produced worldwide today is prepared virtually exclusively from methanol. The second stage of this "indirect" DME synthesis, viz. the preparation of DME from methanol, is based on the known reaction design basis of conversion of methanol into DME and water in the gas phase over an acid catalyst, for example over $Al_2O_3$, in a single-stage fixed-bed reactor. The following chemical reaction takes place here:

$$2CH_3OH \rightleftharpoons CH_3OCH_3 + H_2O, \Delta H = -24 \text{ kJ/mol}$$

The heat of the exothermic reaction is either removed by cooling in the reactor or the gaseous feed methanol is, in the case of adiabatic operation of the reaction, superheated by the heat of the reaction product in a feed heat exchanger. In the case of a cooled reactor, this is typically designed as a tube reactor, with the chemical reaction taking place in the catalyst-filled tubes and the reaction at the same time being cooled by the gaseous feed methanol which is conveyed to the shell side of the reactor and is further preheated there by the heat of reaction.

The version of the methanol-based DME process which is described below as "prior art DME process" is based on the use of a DME reactor. The DME reactor is usually followed by a product work-up using two rectification columns, an DME column and a methanol column for separating off unreacted feed methanol from water, and also an offgas scrubber. This DME process is shown in FIG. 1.

The prior art DME process usually comprises a complicated heat integration, with the hot reaction product being utilized for heating the feed methanol and for operating boilers or for heating streams which are circulated by pumping in the vicinity of the bottom of one of the columns.

There is a continual search for improving the process economics of industrial processes. Possible improvements can relate to the energy efficiency, low purity requirements of the starting materials, higher product purity, productivity and/or the apparatuses used.

The earlier DE 10 2011 114 228 A1, which is not a prior publication, discloses a cooled reactor for preparing dimethyl ether from methanol by heterogeneously catalyzed dehydration. A reactor in which adiabatic heating by means of the heat of reaction liberated in the start zone is firstly carried out, by which means the reaction rate is increased to industrially acceptable values, is used. One of the reactor designs presented comprises a plurality of catalyst beds connected in series. The work-up of the reaction product dimethyl ether is not disclosed.

US 2009/0023958 A1 discloses a process for preparing dimethyl ether from methanol in an adiabatically operated reactor in which two catalyst beds are arranged in series. The process is characterized by the use of selected catalysts in the catalyst beds.

U.S. Pat. No. 4,560,87 A discloses a further process for preparing dimethyl ether and also working up the product obtained. The resulting dimethyl ether is formed in good yield and is obtained in high purity.

It is an object of the present invention to provide an improved process and a plant suitable for this purpose for preparing dimethyl ether, which give a high productivity.

The DME synthesis is an equilibrium reaction. It is independent of or only insignificantly dependent on the pressure. The equilibrium can be shifted in the direction of DME formation by a low working temperature. However, the kinetics of the catalytic reaction at the same time require a minimum working temperature for the chemical reaction to light-off and proceed in a stable manner.

To achieve a high conversion of the equilibrium reaction, it is thus advantageous to work at the lowest possible reactor temperature, which results in a relatively low reactor outlet temperature.

Small DME plants, e.g. for preparing pure DME as propellant, mostly have one cooled reactor. Such plants usually have capacities of from 10 000 to 40 000 metric tons per year. The cooled reactor, designed as a tube reactor with cooling by methanol vapor on the shell of the apparatus, is economically feasible at small to medium plant capacities.

Larger DME plants for producing fuel-grade DME as LPG or diesel substitute usually have capacities of more than 100 000 metric tons per year. The design of such large plants has been known for about ten years, while small plants for producing pure DME have been built for over thirty years. At the construction scale of fuel-grade DME plants, tube reactors are very expensive because of the large number of tubes and because two tube reactors have to be provided in parallel at the largest capacities. Industrially, an adiabatic fixed-bed reactor, which can have, for example, the form of a shaft reactor, is therefore used at such large plant capacities for reasons of lower capital costs.

A disadvantage of the adiabatic mode of operation is that the temperature of the reaction mixture typically increases by more than 100° C. within the reactor. This shifts the reaction equilibrium to a lower methanol conversion compared to a cooled reactor which has a lower outlet temperature. As a result, more unreacted methanol has to be recovered in the methanol column, which significantly increases the capital costs and the operating media costs of this column.

BRIEF DESCRIPTION OF THE DRAWINGS

The present disclosure is described in detail below with reference to the attached drawing figure, wherein.

DETAILED DESCRIPTION

Figure 1:
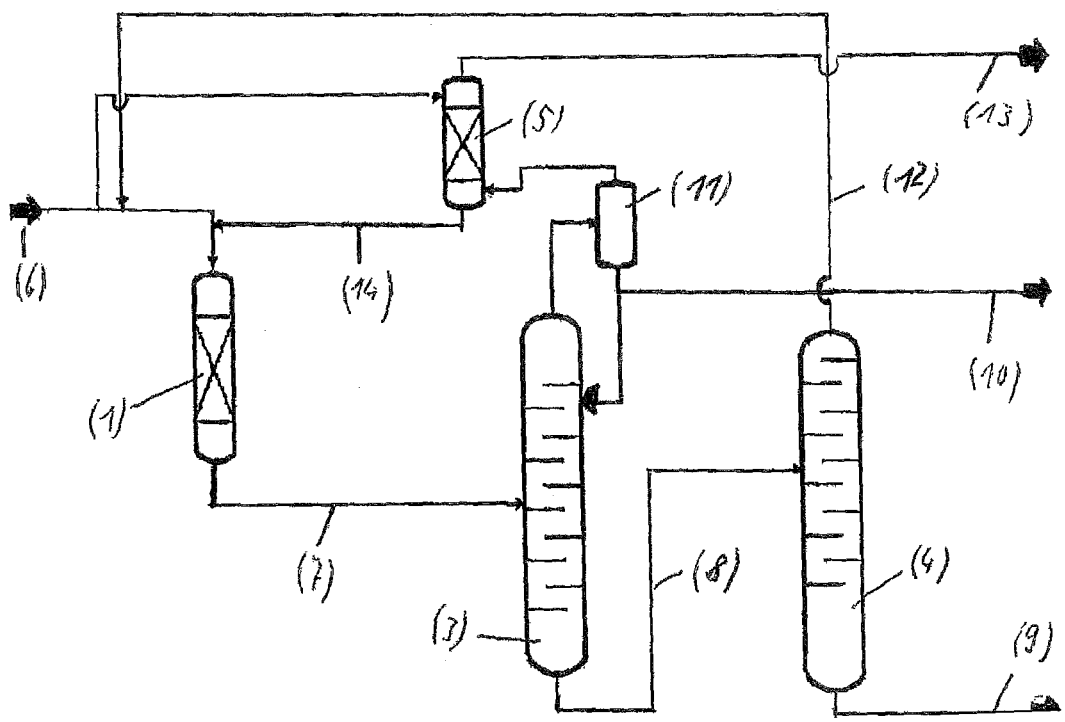
FIG. 1 is schematic diagram depicting a DME process.

To provide a remedy here, the conventional concept of an adiabatic reactor has been improved according to the invention by carrying out the reaction in at least two reaction stages connected in series, of which at least the first is operated adiabatically and the reaction product is cooled between the two reaction stages.

The present invention provides a process for preparing dimethyl ether by catalytic dehydration of methanol and work-up of the dehydration product by distillation, which is characterized in that the catalytic dehydration is carried out in at least two reaction stages connected in series, of which at least the first reaction stage is operated adiabatically and cooling of the reaction product is carried out at least between the first reaction stage and the second reaction stage.

The process of the invention is thus carried out in at least two reaction stages connected in series, of which the first reaction stage or preferably the first and second reaction stages is/are operated adiabatically.

However, it is also possible to provide a larger number of reaction stages connected in series, of which at least one, preferably two and very particularly preferably all, reaction stages are operated adiabatically.

In a preferred process variant, at least one reaction stage consists of a plurality of reactors connected in parallel. Particular preference is given to using a plurality of reactors connected in parallel in all of the reaction stages connected in series.

As an alternative, the process of the invention can also comprise at least two reaction stages, with the first reaction stage being operated adiabatically and one or more downstream reaction stages being operated nonadiabatically, for example isothermally.

Cooling of the reaction mixture is carried out at least between the first reaction stage and the second reaction stage. When more than two reaction stages are present, cooling of the reaction mixture preferably takes place between each reaction stage.

The temperature in the reaction stages of the process of the invention is lower compared to the temperature in the adiabatically operated reactors of the prior art. The temperature in the reaction stages connected in series according to the invention is typically in each case in the range from 200 to 400° C., preferably from 250 to 370° C.

The process of the invention is preferably operated using two adiabatic reaction stages connected in series.

Between the individual reaction stages, the reaction mixture is cooled. Within an adiabatic reaction stage, the reaction temperature increases since the process is exothermic. In general, the reaction mixture is cooled after passage through an adiabatic reaction stage to such an extent that its temperature corresponds approximately to the temperature at which the reaction mixture enters the preceding adiabatic reaction stage. In the case of a reaction stage which is not operated adiabatically, for example an isothermally operated reaction stage, the reaction mixture is cooled to below the entry temperature and DME formation is promoted in this way. The temperature of the reaction mixture is preferably decreased to from 200 to 300° C. between the reaction stages.

Cooling of the reaction mixture can be carried out by use of heat exchangers and/or by introduction of cooling liquid directly into the reaction mixture ("quenching").

Suitable cooling liquids are methanol, DME and/or water, with liquid methanol preferably being used in the first reaction stages and liquid DME or a DME-containing liquid preferably being used in the last reaction stage. The cooling liquid is introduced, e.g. sprayed, into the gaseous reaction mixture between the reaction stages and, as a result of vaporization, brings about effective cooling of the reaction mixture.

Suitable heat exchangers are of all known types, for example helically coiled heat exchangers, shell-and-tube heat exchangers and plate heat exchangers. These are preferably supplied with liquids which originate from the DME plant and can effect cooling of the hot reaction mixture.

Thus, for example, methanol from the methanol column can be used as coolant for the heat exchanger or exchangers.

The various reaction stages of the process of the invention can be realized by means of at least two reactors connected in series, of which at least the first is operated adiabatically. Cooling of the reaction mixture is carried out at least between the first two reactors.

In an alternative variant of the process of the invention, the various reaction stages can be realized in one reactor, with at least the first of the reaction stages being operated adiabatically. Preference is given to using an adiabatically operated reactor which has at least two catalyst beds connected in series. A heat exchanger for intermediate cooling of the reaction mixture from the catalyst bed located upstream is arranged at least between the first and second catalyst beds, preferably between all catalyst beds, and/or cooling liquid is sprayed into the reaction mixture between at least the first two catalyst beds, preferably between all catalyst beds.

Preferred reactors are adiabatically operated fixed-bed reactors.

In the case of nonadiabatic operation, preference is given to using shell-and-tube reactors or fluidized-bed reactors.

As heat exchangers, it is possible to use all known types. Examples are shell-and-tube heat exchangers, helically coiled heat exchangers or plate heat exchangers.

In a preferred variant of the process of the invention, the cooling of the reaction product between the reaction stages is effected by means of a heat exchanger through which vapor of the methanol used for the dehydration is conveyed as cooling medium.

In a particularly preferred variant of the process of the invention, three adiabatically operated reaction stages connected in series are provided and liquid methanol is introduced as coolant into the reaction mixture between the first and second reaction stages and the cooling of the reaction mixture between the second and third reaction stages is effected by means of a heat exchanger through which vapor of the methanol used for the dehydration is preferably conveyed as cooling medium.

This embodiment of the process of the invention is preferably carried out in an adiabatically operated reactor which has three catalyst beds connected in series, a device for introducing liquid methanol into the reaction mixture between the first and second catalyst beds and a heat exchanger, preferably a plate heat exchanger, between the second and third catalyst beds in order to cool the reaction mixture before it enters the third catalyst bed.

In the process of the invention, it is possible to employ the conventional catalysts used for the dehydration of methanol. Preference is given to using an acidic and solid catalyst, preferably aluminum oxide, for the dehydration. As an alternative to aluminum oxide, it is also possible to use other solid acidic catalysts, for example aluminosilicates such as zeolites or titanium dioxide or aluminotitanates.

As a result of the above-described way of carrying out the reaction, the reaction equilibrium is set at a low reactor exit temperature comparable to that of a cooled reactor and a higher methanol conversion and a lower amount of recirculated methanol are thus achieved. The throughput through the methanol column is significantly reduced thereby.

In a preferred embodiment of the process of the invention, the reaction mixture coming from the last reaction stage is worked up in a DME column in which dimethyl ether is separated off from the reaction mixture by distillation to leave a bottom product which is transferred from the DME column into a methanol column where it is separated by distillation into a methanol stream and a water-containing bottom product. The methanol stream obtained is preferably recirculated to one or more of the DME reaction stages.

The process of the invention has a number of advantages compared to the prior art DME processes. In the process of the invention, up to about 30% less methanol is distilled off in the methanol column of the two-stage reaction concept. The amount of recirculated methanol is thus reduced by up to about 70% of the value obtained in the prior art DME processes because of the higher methanol conversion in the two-stage reaction. As a result, the diameter of the methanol column can be reduced in the process of the invention and costs incurred for operating media in the materials separation can be saved.

The process of the invention results in a lower reactor outlet temperature compared to other adiabatic processes and therefore permits a higher methanol equilibrium conversion, for example up to 88%.

In summary, the process of the invention thus leads to:
a smaller amount of circulated methanol (about 30% smaller)
and thus smaller equipment (for example, the diameter of the methanol column becomes about 17% smaller)
and to lower operating costs for materials separation (saving of cooling water of about 20%, saving of steam of about 40%).

Additional costs are incurred as a result of the use of a second reactor and as a result of a somewhat greater amount of catalyst needed.

Looking at the overall economics of a large DME plant of 800 000 metric tons per year, on the basis of a comparison of capital costs and operating costs of the plant over a life of 20 years, the two-stage reaction is more economical than the "standard" DME plant having one adiabatic reactor.

Product income and raw materials costs are the same in both variants since the amounts of DME and methanol are identical. The improved economics thus result from the lower total costs.

The invention also provides an apparatus for preparing dimethyl ether by catalytic dehydrogenation of methanol, which comprises the elements:
A) at least two DME reactors (1a, 1b) connected in series, of which at least the first DME reactor is operated adiabatically,
B) a cooling apparatus (2) arranged between at least the first DME reactor and the second DME reactor for cooling the reaction mixture from the reactor (1a) located upstream of the cooling apparatus (2),
C) a DME column (3) connected to the last reactor (1b) for separating the dimethyl ether from the reaction mixture, and
D) a methanol column (4) connected to the bottom of the DME column (3) for separating the reaction mixture which has been freed of the dimethyl ether into methanol and water.

An alternative embodiment of the invention provides an apparatus for preparing dimethyl ether by catalytic dehydrogenation of methanol, which comprises the elements:
A') at least one DME reactor in which at least two reaction stages connected in series, of which at least the first reaction stage is operated adiabatically, are arranged,
B') a cooling apparatus (2) arranged between at least the first reaction stage and the second reaction stage for cooling the reaction mixture from the reaction stage located upstream of the cooling apparatus,
C') a DME column (3) connected to the last reaction stage for separating the dimethyl ether from the reaction mixture, and
D) a methanol column (4) connected to the bottom of the DME column (3) for separating the reaction mixture which has been freed of the dimethyl ether into methanol and water.

In a preferred embodiment, the apparatus of the invention has an adiabatically operated DME reactor in which two catalyst beds connected in series are provided and a cooling apparatus which serves for intermediate cooling of the reaction mixture from the catalyst bed located upstream. The adiabatically operated reactor is, in particular, a vertical shaft reactor. The cooling apparatus (2) is a heat exchanger and/or an apparatus for introducing cooling liquid into the reaction mixture.

In a further preferred embodiment of the apparatus of the invention, methanol from the methanol column (4) is recirculated to the first adiabatically operated DME reactor (1a) or to the first adiabatically operated reaction stage of the DME reactor.

In a further preferred embodiment of the apparatus of the invention, a heat exchanger through which vapor of the methanol used for the dehydration is conveyed as cooling medium is used as cooling apparatus (2).

The capital costs in the case of a two-stage reaction can be reduced further by the two reaction stages not being formed by two apparatuses (two reactors) but being realized in one reactor. Such an integrated vertical shaft reactor comprises two or even more catalyst beds and one or more intermediate cooling stages using one or more built-in heat exchangers, preferably plate heat exchangers, or by introducing cooling liquid, preferably methanol. The heat exchangers are particularly preferably supplied with vapor of the feed methanol as cooling medium.

Figure 2:
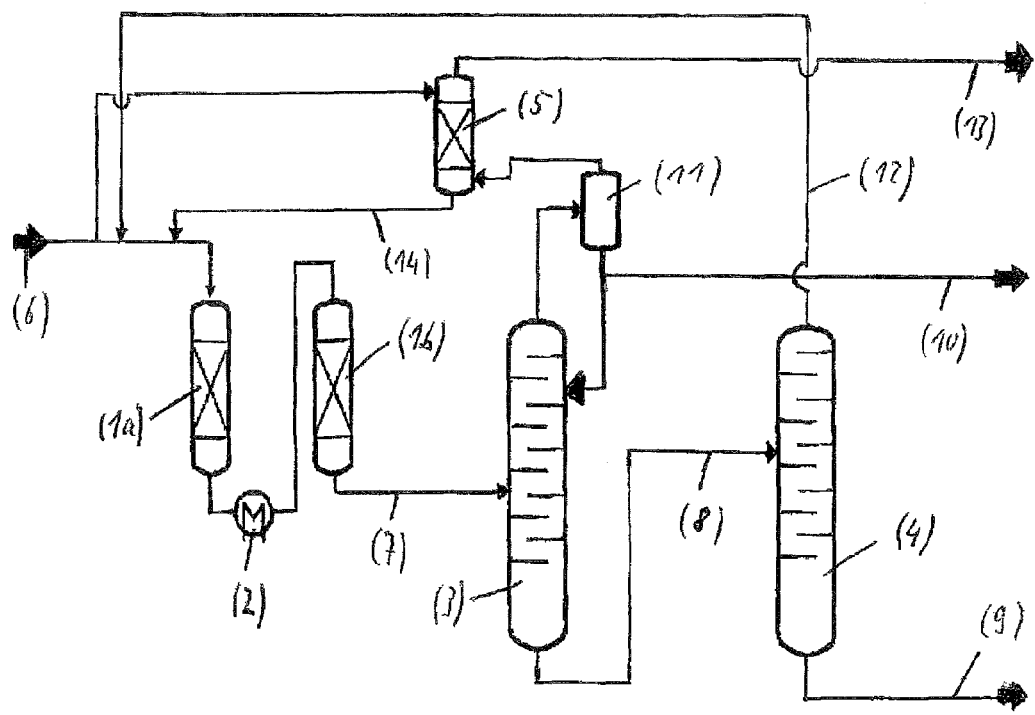
FIG. 2 is a schematic diagram of an embodiment of a process of the present disclosure.

FIGS. 1 and 2 describe, by way of example and schematically, a process according to the prior art and a variant of the process of the invention.

FIG. 1 schematically shows the known DME process. The feed methanol (6) is vaporized and superheated and then fed into the DME reactor (1) at a temperature of at least 250° C. The equilibrium reaction of methanol to form DME and water takes place over an acid catalyst, at a pressure of about 12-14 bar(a) and with a methanol conversion of about 83%. The reaction product (7) leaves the DME reactor (1) at about 370° C. and is cooled by heat integration, for example firstly by heat exchange with the feed methanol vapor and then by heating of a boiler or by heating of streams which are circulated by pumping in the vicinity of the bottom of one of the columns. The reaction product (7) which has been cooled in this way is introduced into the DME column (3). In this DME column (7), the DME is separated off as liquid overhead product at a pressure of about 10-12 bar(a) using cooling water in the overhead condenser and fed into a runback vessel (11). Liquid DME product (10) is taken off from this and discharged from the plant or part thereof is recirculated to the DME column. The gas phase from the runback vessel (11) is fed into a DME absorber (5). In addition, part of the feed methanol (6) is fed into the DME absorber (5). In the DME absorber (5), incondensable gases (13) consisting of a small amount of dissociation gas ($H_2$, CO, $CO_2$ and $CH_4$) and DME are scrubbed with methanol in order to recover the DME, and the liquid product (14) from the DME absorber (5) is fed to the DME reactor (1). The bottom product (8) from the DME column (3) is separated into methanol (12) and water (9) in the methanol column (4) which is operated at a slight superatmospheric pressure. In the methanol column (4), the unreacted methanol (12) is recovered and this is fed back into the process. The remaining amount of water in the recirculated methanol is subject matter of optimization since it has effects on the costs of methanol column (4) and DME reactor (1). A higher water content in the circulated methanol has an unfavorable influence on the conversion of methanol via the reaction equilibrium and in addition means that the chemical reaction has to be operated at a higher entry temperature, which in turn has unfavorable effects on the equilibrium since the methanol conversion decreases at higher temperature.

The process indicated is described in Ullmann's Encyclopedia of Industrial Chemistry, Fifth Completely Revised Edition, Volume A8, pages 541 to 544, of 1987 and also in numerous patent documents such as U.S. Pat. No. 4,802,958 and EP 0 270 852 A2.

FIG. 2 schematically shows a variant of the process of the invention. The feed methanol (6) is vaporized and superheated and then fed into a first DME reactor (1a) at a temperature of about 250° C. The equilibrium reaction of methanol to form DME and water takes place over an acid catalyst, at a pressure of about 12-14 bar(a) and with a methanol conversion of about 83%. The reaction product from the first reaction stage is cooled by heat integration from about 370° C. to 250° C., e.g. in a heat exchanger (2) which cools the product and at the same time superheats the feed methanol vapor (6). The cooled reaction product is fed at 250° C. into the second DME reactor (1b) where further methanol is reacted as a result of the more favorable position of the equilibrium at lower temperature. The reaction product (7) leaves the second DME reactor (1b) at a temperature of about 260° C. As a result of the use of the second DME reactor, the total methanol conversion is now increased to about 88%. The amount of unreacted methanol is at the same time reduced by 30%.

After cooling (not shown in FIG. 2) of the DME product (7) from the second reaction stage by heat exchange, once again using feed methanol (6) and/or by heating of a boiler or by heating of streams which are circulated by pumping in the vicinity of the bottom of one of the columns, this is fed into the DME column (3). In this DME column (3), the DME is separated off as liquid overhead product using cooling water in the overhead condenser at a pressure of about 10-12 bar(a) and fed into a runback vessel (11). Liquid DME product (10) is taken off from this and discharged from the plant or part thereof is recirculated to the DME column. The gas phase from the runback vessel (11) is fed to a DME absorber (5). In addition, part of the feed methanol (6) is fed into the DME absorber (5). In the DME absorber (5), incondensable gases consisting of a small amount of dissociation gas ($H_2$, CO, $CO_2$ and $CH_4$) and DME are scrubbed with methanol in order to recover the DME, and the liquid product (14) from the DME absorber (5) is fed to the first DME reactor (1a). The bottom product (8) from the DME column (3) is separated into methanol (12) and water (9) in the methanol column (4) which is operated at a slightly superatmospheric pressure. In the methanol column (4), the unreacted methanol (12) is recovered and this is fed back into the process.

The invention claimed is:

1. A method for preparing dimethyl ether, comprising:
performing catalytic dehydration of methanol in at least a first reaction stage, a second reaction stage, and a third reaction stage that are connected in series, so as to produce a dehydration product, said performing catalytic dehydration step comprising:
operating the first reaction stage adiabatically,
cooling a reaction product from the first reaction stage by quenching the reaction product before it is further reacted downstream in the second reaction stage, and
cooling the reaction product from the second stage by use of a heat exchanger before it is further reacted downstream in the third reaction stage; and
distilling the dehydration product.

2. The method of claim 1, wherein said first and second reaction stages are both operated adiabatically.

3. The method of claim 1, wherein said second reaction stage is downstream of said first reaction stage and operated nonadiabatically.

4. The method of claim 1, wherein the second reaction stage is operated adiabatically, and wherein a reaction temperature in the first and second reaction stages is between 200 to 400° C.

5. The method of claim 1, wherein during said cooling step between the first and second reaction stages, a temperature of the reaction product is decreased to a temperature of between 200° C. and 300° C.

6. The method of claim 1, wherein the reaction stages of said performing catalytic dehydration step are carried out in at least two adiabatically operated reactors connected in series, and wherein said cooling of the reaction product is performed between the at least two adiabatically operated reactors.

7. The method of claim 1, wherein said performing catalytic dehydration is carried out in an adiabatically operated reactor having at least a first upstream catalyst bed corresponding to the first catalyst stage and a second downstream catalyst bed corresponding to the second catalyst stage, the first and second catalyst beds being connected in series, and wherein said cooling step is performed in a cooling apparatus disposed between the first and second catalyst beds for intermediate cooling of the reaction product from the first catalyst bed located upstream.

8. The method of claim 7, wherein said cooling step is at least partially performed by at least one of heat exchangers or by introduction of cooling liquid directly into the reaction product.

9. The method of claim 8, wherein the cooling liquid is one of methanol, DME, water, or mixtures thereof.

10. The method of claim 1, wherein quenching the reaction product from the first reaction stage comprises introducing liquid methanol as a coolant into the reaction product between the first and second reaction stages, wherein vapor of the methanol from the dehydration step is conveyed as a cooling medium through the heat exchanger.

11. The method of claim 1, wherein said step of performing catalytic dehydration is performed in an adiabatically operated reactor having a first, a second, and a third catalyst bed connected in series, wherein the reaction product from the first catalyst bed is quenched by introducing liquid methanol into the reaction product between the first and the second catalyst bed, wherein the heat exchanger is disposed between the second and third catalyst beds and cools the reaction product from the second catalyst bed before it enters the third catalyst bed.

12. The method of claim 1, wherein said cooling step is performed by a heat exchanger through which vapor of the methanol used for the dehydration is conveyed as cooling medium.

13. The method of claim 1, wherein an acidic and solid catalyst is the catalyst used in the step of performing catalytic dehydration.

14. The method of claim 1, wherein said step of distilling the dehydration product comprises:
- in a DME column, distilling the reaction product coming from a last reaction stage of said catalytic dehydration to separate off dimethyl ether from a bottom product;
- transferring the bottom product from the DME column into a methanol column; and
- in the methanol column, distilling the bottom product to separate off a methanol stream from a water-containing bottom product.

* * * * *